United States Patent [19]
Elshourbagy et al.

[11] Patent Number: 5,858,716
[45] Date of Patent: Jan. 12, 1999

[54] H2CAA71 POLYNUCLEOTIDES

[75] Inventors: Nabil A. Elshourbagy, West Chester; Xiaotong Li, Devon; Derk J. Bergsma, Berwyn, all of Pa.

[73] Assignee: SmithKline Beecham Corporation, Philadelphia, Pa.

[21] Appl. No.: 866,757

[22] Filed: May 30, 1997

[51] Int. Cl.$^6$ ............................ C12N 15/09; C07K 14/705
[52] U.S. Cl. ................... 435/69.1; 536/23.5; 435/252.3; 435/254.11; 435/320.1; 435/325; 435/172.1; 935/1
[58] Field of Search ..................................... 435/69.1, 325, 435/320.1, 252.3, 254.11, 172.1; 536/23.5; 935/1

[56] References Cited

PUBLICATIONS

George et al., Macromolecular Sequencing and Synthesis, 127–149, 1988, Alan K. Liss, Inc. New York.

*Primary Examiner*—Sally P. Teng
*Attorney, Agent, or Firm*—Ratner & Prestia; Elizabeth Hecht; William T. King

[57] ABSTRACT

Novel 7TM receptor (H2CAA71) polypeptides and polynucleotides and methods for producing such polypeptides by recombinant techniques are disclosed. Also disclosed are methods for utilizing Novel 7TM receptor (H2CAA71) polypeptides and polynucleotides in the design of protocols for the treatment of infections such as bacterial, fungal, protozoan and viral infections, particularly infections caused by HIV-1 or HIV-2; pain; cancers; anorexia; bulimia; asthna; Parkion's disease; acute heart failure; hypotension; hypertension; uinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others and diagnostic assays for such conditions.

16 Claims, No Drawings

5,858,716

H2CAA71 POLYNUCLEOTIDES

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to G-protein coupled receptor family, hereinafter referred to as Novel 7TM receptor (H2CAA71). The invention also relates to inhibiting or activating the action of such polynucleotides and polypeptides.

BACKGROUND OF THE INVENTION

It is well established Mat many medically significant biological processes are mediated by proteins participating in signal transduction pathways that involve G-proteins and/or second messengers, e.g., cAMP (Lefkowitz, Nature, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA, 1987, 84:46–50; Kobilka, B. K., et al., Science, 1987, 238:650–656; Bunzow, J. R., et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelial, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM 1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form a polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317–331) Different G-protein a-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7TM) receptors have been successfully introduced onto the market.

This indicates that these receptors have an established, proven history as therapeutic targets. Clearly there is a need for identification and characterization of further receptors which can play a role in preventing, ameliorating or correcting dysfunctions or diseases, including, but not limited to, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

SUMMARY OF THE INVENTION

In one aspect, the invention relates to Novel 7TM receptor (H2CAA71) polypeptides and recombinant materials and methods for their production. Another aspect of the invention relates to methods for using such Novel 7TM receptor (H2CAA71) polypeptides and polynucleotides. Such uses include the treatment of infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies;

benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. In still another aspect, the invention relates to methods to identify agonists and antagonists using the materials provided by the invention, and treating conditions associated with Novel 7TM receptor (H2CAA71) imbalance with the identified compounds. Yet another aspect of the invention relates to diagnostic assays for detecting diseases associated with inappropriate Novel 7TM receptor (H2CAA71) activity or levels.

DESCRIPTION OF THE INVENTION

Definitions

The following definitions are provided to facilitate understanding of certain terms used frequently herein.

"Novel 7TM receptor (H2CAA71)" refers, among others, to a polypeptide comprising the amino acid sequence set forth in SEQ ID NO:2, or an allelic variant thereof "Receptor Activity" or "Biological Activity of the Receptor" refers to the metabolic or physiologic function of said Novel 7TM receptor (H2CAA71) including similar activities or improved activities or these activities with decreased undesirable side-effects. Also included are antigenic and immunogenic activities of said Novel 7TM receptor (H2CAA71).

"Novel 7TM receptor (H2CAA7 1) gene" refers to a polynucleotide comprising the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann N.Y. Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to Novel 7TM receptor (H2CAA71) polypeptides. The Novel 7TM receptor (2CAA71) polypeptides include the polypeptide of SEQ ID NO:2; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO:2. Furthermore, those with at least 97–99% are highly preferred. Also included within Novel 7TM receptor (H2CAA71) polypeptides are polypeptides having the amino acid sequence which have at least 80% identity to the polypeptide having the amino acid sequence of SEQ ID NO:2 over its entire length, and still more preferably at least 90% identity, and even still more preferably at least 95% identity to SEQ ID NO:2. Furthermore, those with at least 97–99% are highly preferred. Preferably Novel 7TM receptor (H2CAA71) polypeptides exhibit at least one biological activity of the receptor.

The Novel 7TM receptor (H2CAA71) polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the Novel 7TM receptor (H2CAA71) polypeptides are also included in the invention. A fragment is a polypeptide having an amino acid sequence that entirely is the same as part, but not all, of the amino acid sequence of the aforementioned Novel 7TM receptor (H2CAA71) polypeptides. As with Novel 7TM receptor (H2CAA71) polypeptides, fragments may be "free-standing," or comprised within a larger polypeptide of which they form a part or region, most preferably as a single continuous region. Representative examples of polypeptide fiagments of the invention, include, for example, fragments from about amino acid number 1–20, 21–40, 41–60, 61–80, 81–100, and 101 to the end of Novel 7TM receptor (H2CAA71) polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of Novel 7TM receptor (H2CAA71) polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterieed by structural or functional attributes such as fragments that comprise alpha-helix and alpha-helix forming regions, beta-sheet and beta-sheet-formiing regions, turn and turn-forming regions, coil and coil-formiing regions, hydrophilic regions, hydrophobic regions, alpha amphipathic regions, beta amphipathic regions, flexible regions, surface-forning regions, substrate binding region, and high antigenic index regions. Other preferred fragments are biologically active fragments. Biologically active frgments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Izu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The Novel 7TM receptor (H2CAA71) polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to Novel 7TM receptor (H2CAA71) polynucleotides. Novel 7TM receptor (H2CAA71) polynucleotides include isolated polynucleotides which encode the Novel 7TM receptor (H2CAA71) polypeptides and fragments, and polynucleotides closely related thereto. More specifically, Novel 7TM receptor (H2CAA71) polynucleotide of the invention include a polynucleotide comprising the nucleotide sequence set forth in SEQ ID NO:1 encoding a Novel 7TM receptor (H2CAA71) polypeptide of SEQ ID NO:2, and polynucleotide having the particular sequence of SEQ ID NO:1. Novel 7TM receptor (H2CAA71) polynucleotides further include a polynucleotide comprising a nucleotide sequence that has at least 80% identity to a nucleotide sequence encoding the Novel 7TM receptor (H2CAA71) polypeptide of SEQ ID NO:2 over its entire length, and a polynucleotide that is at least 80% identical to that having SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under Novel 7TM receptor (H2CAA71) polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such Novel 7TM receptor (H2CAA71) polynucleotides.

Novel 7TM receptor (H2CAA71) of the invention is structurally related to other proteins of the G-protein coupled receptor family, as shown by the results of sequencing the cDNA of Table 1 (SEQ ID NO:1) encoding human Novel 7TM receptor (H2CAA7 1). The cDNA sequence of SEQ ID NO:1 contains an open reading frame (nucleotide numbers 483 to 2415) encoding a polypeptide of 644 amino acids (SEQ ID NO:2). The amino acid sequence of Table 2 (SEQ ID NO:2) has about 27% identity (using FASTA) in 571 amino acid residues with Bovine follicle stimulating hormone receptor. Houde A 1994 Mol. Reprod. Dev.,39, 127–135. The nucleotide sequence of Table 1 (SEQ ID NO:1) has about 60% identity (using FASTA) in 80 nucleotide residues with Bovine follicle stimulating hormone receptor Houde A 1994 Mol. Reprod. Dev.,39, 127–135.

TABLE 1[a]

| | | | | |
|---|---|---|---|---|
| 1 GCTTCCATCC | TAATACAACT | CACTATAGGG | CTCGAGCGGC | CGCCCGGGCA |
| 51 GGTGCTTGAC | GGAGGTGCCT | GTGCACCCCC | TCAGCAATCT | GCCCACCCTA |
| 101 CAGGCGCTGA | CCCTGGCTCT | CAACAAgATC | TCAAGCATCC | CTgACTTTGC |
| 151 ATTTACCAAC | CTTTCAAGCC | TGGTAgTTCT | GCATCTTCAT | AACAATAAAA |
| 201 TTAgAAGCCT | GAGTCAACAC | TGTTGTGATG | GACTAgATaA | CCTGGAGACC |
| 251 TTAgACTTGA | ATTATAATAA | CTTGGGGGAA | TTTCCTCAGG | CTATTAAAGC |
| 301 CCTTCCTAGC | CTTAAAgAGC | TAGGATTTCA | TAGTAATTCT | ATTTCTGTTA |
| 351 TCCCTATGGA | GCATGGGATG | GTAATCCACT | CTTAAgAACT | ATACATTTGT |
| 401 ATGATAATCC | TCTGTCTTTT | GTGGGGAACT | CAGCATTTCA | CAAttTATCT |
| 451 GATCTTCATT | CCCTAGTCAT | TCGTGGTGCA | AGCATGGTGC | AGCAGTTCCC |
| 501 CAATCTTACA | GGAACTGTCC | ACCTGGAAAG | TCTGACTTTG | ACAGGTACAA |
| 551 AGATAAGCAG | CATACCTAAT | AATTTGTGTC | AAGAACAAAA | GATGCTTAGG |
| 601 ACTTTGGACT | TGTCTTACAA | TAATATAAGA | GACCTTCCAA | GTTTTAATGG |
| 651 TTGCCATGCT | CTGGAAGAAA | TTTCTTTACA | GCGTAATCAA | ATCTACCAAA |
| 701 TAAAGGAAGG | CACCTTTCAA | GGCCTGATAT | CTCTAAGGAT | TCTAGATCTG |
| 751 AGTAGAAACC | TGATACATGA | AATTCACAGT | AGAGCTTTTG | CCACACTTGG |
| 801 GCCAATAACt | AACCTAGAtG | TAAGTTTCAA | tGAATTAACT | TCcTTTCCtA |
| 851 CGGAAGGCCt | GAATGGGCTA | AATCAACTGA | AACTGGTGGG | CAACTTCAAG |
| 901 CTGAAAGAAG | CCTTAGCAGC | AAAAGACTTt | GTTAACCTCa | GGTCTTTATC |
| 951 AGTACCATAT | GCTTATCAGT | GCTGTGCATT | TtGGGGTTGT | GACTCTTATG |
| 1001 CAAATTTAAA | CACAGAAGAT | AACAGCCTCC | AGGACCACAG | TGTGGCACAG |
| 1051 GAGAAAGGTA | CTGCTGATGC | AGCAAATGTC | ACAAGCACTC | TTGAAAATGA |
| 1101 AGAACATAGT | CAAATAATTA | TCCATTGTAC | ACCTTCAACA | GGTGCTTTTA |
| 1151 AGCCCTGTGA | ATATTTACTG | GGAAGCTGGA | TGATTCGTCT | TACTGTGTGG |
| 1201 TTCATTTTCT | TGGTTGCATT | ATTTTTCAAC | CTGCTTGTTA | TTTTAACAAC |
| 1251 ATTTGCATCT | TGTACATCAC | TGCCTTCGTC | CAAATTGTTT | ATAGGCTTGA |
| 1301 TTTCTGTGTC | TAACTTATTC | ATGGGAATCT | ATACTGGCAT | CCTAACTTTT |
| 1351 CTTGATGCTG | TGTCCTGGGG | CAGATTCGCT | GAATTTGGCA | TTTGGTGGGA |
| 1401 AACTGGCAGT | GGCTGCAAAG | TAACTGGGTT | TCTTGCAgTT | TTCTCCTCAG |
| 1451 AAAGTGCCAT | ATTTTTATTA | ATGCTAgCAA | CTGTCGAAAG | AAgCTTATCT |
| 1501 GCAAAAGATA | TAATGAAAAA | TGGGAAGAGC | AATCATCTCA | AACAGTTCCG |
| 1551 GGTTGCTGCC | CTTTTGGCTT | TCCTAGGTGC | TACAGTAACA | GGCTGTTTTC |
| 1601 CCCTTTTCCA | TAGAGGGGAA | TATTCTGCAT | CACCCCTTTG | TTTGCCATTT |

TABLE 1ª-continued

| | | | | |
|---|---|---|---|---|
| 1651 CCTACAGGTG | AAACGCCATC | ATTAGGATTC | ACTGTAACGT | TAGTGCTATT |
| 1701 AAACTCACTA | GCATTTTTAT | TAATGGCCGT | TATCTACACT | AAGCTATACT |
| 1751 GCAACTTGGA | AAAAGAGGAC | CTCTCAGAAA | ACTCACAATC | TAGCATGATT |
| 1801 AAGCATGTCG | CTTGGCTAAT | CTTCACCAAT | TGCATCTTTT | TCTGCCCTGT |
| 1851 GGCGTTTTTT | TCATTTGCAC | CATTGATCAC | TGCAATCTCT | ATCAGCCCCG |
| 1901 AAATAATGAA | GTCTGTTACT | CTGATATTTT | TTCCATTGCC | TGCTTGCCTG |
| 1951 AATCCAGTCC | TGTATGTTTT | CTTCAACCCA | AAGTTTAAAG | AAGACTGGAA |
| 2001 GTTACTGAAG | CGACGTGTTA | CCAAGAAAAG | TGGATCAGTT | TCAGTTTCCA |
| 2051 TCAGTAGCCA | AGGTGGTTGT | CTGGAACAGG | ATTTCTACTA | CGACTGTGGC |
| 2101 ATGTACTCAC | ATTTGCAGGG | CAACCTGACT | GTTTGCGACT | GCTGCGAATC |
| 2151 GTTTCTTTTA | ACAAAGCCAG | TATCATGCAA | ACACTTGATA | AAATCACACA |
| 2201 GCTGTCCTGC | ATGGGCAGTG | GCTTCTTGCC | AAAGACCTGA | GGGCTACTGG |
| 2251 TCCGACTGTG | GCACACAGTC | GGCCCACTCT | GATTATGCAG | ATGAAGAAGA |
| 2301 TTCCTTTGTC | TCAGACAGTT | CTGACCAGGT | GCAGGCCTGT | GGACGAGCCT |
| 2351 GCTTCTACCA | GAGTAGAGGA | TTCCCTTTGG | TGCGCTATGC | TTACAATCTA |
| 2401 CCAAGAGTTA | AAGACTGAAC | TACTGTGTGT | GTAACCGTTT | CCCCCGTCAA |
| 2451 CCAAAATCAG | TGTTTATAGA | GTGAACCCTA | TTCTCATCTT | TCATCTGGGA |
| 2501 AGCACTTCTG | TAATCACTGC | CTGGTGTCAC | TTAGAAGAAG | GAGAGGTGGC |
| 2551 AGTTTATTTC | TCAAACCAGT | CATTTTCAAA | GAACAGGTGC | CTAAATTATA |
| 2601 AATTGGTGAA | AAATGCAATG | TCCAAGCAAT | GTATGATCTG | TTTGAAACAA |
| 2651 ATATATGACT | TGAAAAGGAT | CTTAGGTGTA | GTAGAGCAAT | ATAATGTTAG |
| 2701 TtTTTTCTGA | TCCATAAGAA | GCAAATTTAT | ACCTATTTGT | GTATTAAGCA |
| 2751 CAAGATAAAG | AACAGCTGTT | AATATTTTTT | AAAAATCTAT | TTTAAAATGT |
| 2801 GATTTTCTAT | AACTGAACAA | AATATCTTGC | TAATTTTACC | TAATGTTTCA |
| 2851 TCCTTAATCT | CAGGACAACT | TACTGCAGGG | CCAAAAAAGG | GACTGTCCCA |
| 2901 GCTAGAACTG | TGAGAGTATA | CATAGGCATT | ACTTTATTAT | GTTTTCACTT |
| 2951 GCCATCCTTG | ACATAAGAGA | ACTATAAATT | TTGTTTAAGC | AATTTATAAA |
| 3001 TCTAAAACCT | GAAGATGTTT | TTAAAACAAT | ATTAACAGCT | GTTAGGTTAA |
| 3051 AAAAATAGCT | GGACATTTGT | TTTCAGTCAT | TATACATTGC | TTTGGTCCAA |
| 3101 TCAGTAATTT | TTTCTTAAGT | GTTTTGTGAT | TACACTACTA | GAAAAAAAGT |
| 3151 AAAAGGCTAA | TTGCTGTGTG | GGTTTAGTCG | ATTTGGCTAA | ACTACTAACT |
| 3201 AATGTGGGGG | TTTAATAGTA | TCTGAGGGAT | TTGGTGGCTT | CATGTAATGT |
| 3251 TCTCATTAAT | GAATACTTCC | TAATATCGTT | GGCTCTACTA | ATATTTTCCA |
| 3301 ATTTGCTGGG | ATGTCACCTA | GCAATAGCTT | GGATTATATA | GAAAGTAAAC |
| 3351 TGTGGTCAAT | ACTTGCATTT | AATTAGACGA | AACGGGGAGT | AATTATGACA |
| 3401 CGAAGTACTT | ATGTTTATTT | CTTAGTGAGC | TGGATTATCT | TGAACCTGTG |
| 3451 CTATTAAATG | GAAATTTCCA | TACATCTTCC | CCATACTATT | TTTTATAAAA |
| 3501 GAGCCTATTC | AATAGCTCAG | AGGTTGAACT | CTGGTTAAAC | AAGATAATAT |
| 3551 GTTATTAATA | AAAATAGAAG | AAGAAAGAAT | AAAGCTTAGT | CCTGTGTCTT |
| 3601 TAAAAATTAA | AAATTTTACT | TGATTCCCAT | CTATGGGCTT | TAGACCTATT |
| 3651 ACTGGGTGGA | GTCTTAAAGT | TATAATTGTT | CAATATGTTT | TTTGAACAGT |
| 3701 GTGCTAAATC | AATAGCAAAC | CCACTGCCAT | ATTAGTTATT | CTGAATATAC |
| 3751 TAAAAAAATC | CAGCTAGATT | GCAGTTTAAT | AATTAAACTG | TACATACTGT |
| 3801 GCATATAATG | AATTTTTATC | TTATGTAAAT | TATTTTTAGA | ACACAAGTTG |
| 3851 GGAAATGTGG | CTTCTGTTCA | TTTCGTTTAA | TTAAAGCTAC | CTCCTAAACT |
| 3901 ATAGTGGCTG | CCAGTAGCAG | ACTGTTAAAT | TGTGGTTTAT | ATACTTTTTG |
| 3951 CATTGTAAAT | AGTCTTTGTT | GTACATTGTC | AGTGTAATAA | AAACAGAATC |
| 4001 TTTGTATATC | AAAATCATGT | AGTTTGTATA | AAATGTGGGA | AGGATTTATT |
| 4051 TACAGTGTGT | TGTAATTTTG | TAAGGCCAAC | TATTTACAAG | TTTTAAAAAT |
| 4101 TGCTATCATG | TATATTTACA | CATCTGATAA | ATATTAAATC | ATAACTTGGT |
| 4151 AAGAAACTCC | TAATTAAAAG | GTTTTTTCCA | AAAAAAAAAA | AAAAAAAAAA |
| 4201 AAA | | | | |

ªA nucleotide sequence of a human Novel 7TM receptor (H2CAA71) (SEQ ID NO: 1).

TABLE 2[b]

| | | | | |
|---|---|---|---|---|
| 1 MVQQFPNLTG | TVHLESLTLT | GTKISSIPNN | LCQEQKMLRT | LDLSYNNIRD |
| 51 LPSFNGCHAL | EEISLQRNQI | YQIKEGTFQG | LISLRILDLS | RNLIHEIHSR |
| 101 AFATLGPITN | LDVSFNELTS | FPTEGLNGLN | QLKLVGNFKL | KEALAAKDFV |
| 151 NLRSLSVPYA | YQCCAFWGCD | SYANLNTEDN | SLQDHSVAQE | KGTADAANVT |
| 201 STLENEEHSQ | IIIHCTPSTG | AFKPCEYLLG | SWMIRLTVWF | IFLVALFFNL |
| 251 LVILTTFASC | TSLPSSKLFI | GLISVSNLFM | GIYTGILTFL | DAVSWGRFAE |
| 301 FGIWWETGSG | CKVTGFLAVF | SSESAIFLLM | LATVERSLSA | KDIMKNGKSN |
| 351 HLKQFRVAAL | LAFLGATVTG | CFPLFHRGEY | SASPLCLPFP | TGETPSLGFT |
| 401 VTLVLLNSLA | FLLMAVIYTK | LYCNLEKEDL | SENSQSSMIK | HVAWLIFTNC |
| 451 IFFCPVAFFS | FAPLITAISI | SPEIMKSVTL | IFFPLPACLN | PVLYVFFNPK |
| 501 FKEDWKLLKR | RVTKKSGSVS | VSISSQGGCL | EQDFYYDCGM | YSHLQGNLTV |
| 551 CDCCESFLLT | KPVSCKHLIK | SHSCPALAVA | SCQRPEGYWS | DCGTQSAHSD |
| 601 YADEEDSFVS | DSSDQVQACG | RACFYQSRGF | PLVRYAYNLP | RVKD |

[b]An amino acid sequence of a human Novel 7TM receptor (H2CAA71) (SEQ ID NO: 2).

One polynucleotide of the present invention encoding Novel 7TM receptor (H2CAA71) may be obtained using standard cloning and screening, from a cDNA library derived from mRNA in cells of Human placenta using the expressed sequence tag (EST) analysis (Adams, M. D., et al. Science (1991) 252:1651–1656; Adams, M. D. et al., Nature, (1992) 355:632–634; Adams, M. D., et al., Nature (1995) 377 Supp:3–174). Polynucleotides of the invention can also be obtained from natural sources such as genomic DNA libraries or can be synthesized using well known and commercially available techniques.

The nucleotide sequence encoding Novel 7TM receptor (H2CAA71) polypeptide of SEQ ID NO:2 may be identical to the polypeptide encoding sequence contained in Table 1 (nucleotide number 483 to 2415 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of Novel 7TM receptor (H2CAA7 1) polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding Novel 7TM receptor (H2CAA71) variants comprising the amino acid sequence of Novel 7TM receptor (H2CAA71) polypeptide of Table 2 (SEQ ID NO:2) in which several, 5–10, 1–5, 1–3, 1–2 or 1 amino acid residues are substitute or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are identical or sufficiently identical to a nucleotide sequence contained in SEQ ID NO:1 or a fragment thereof, may be used as hybridization probes for cDNA and genomic DNA, to isolate full length cDNAs and genomic clones encoding Novel 7TM receptor (H2CAA71) and to isolate cDNA and genomic clones of other genes that have a high sequence similarity to the Novel 7TM receptor (H2CAA71) gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding Novel 7TM receptor (H2CAA71) polypeptide comprises the steps of screening an appropriate library under stingent hybridization conditions with a labeled probe having the SEQ ID NO:1 or a fragment thereof, and isolating full-length cDNA and genomic clones containing said polynucleotide sequence. Thus in another aspect, Novel 7TM receptor (H2CAA71) polynucleotides of the present invention further include a nucleotide sequence comprising a nucleotide sequence that hybridizes under stringent conditions to a nucleotide sequence having SEQ ID NO:1 or a fragment thereof. Also included with Novel 7TM receptor (H2CAA71) polypeptides are polypeptides comprising amino acid sequences encoded by a nucleotide sequence obtained by the above hybridization condition. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA, followed by washing the filters in 0×SSC at about 650° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, *BASIC METHODS IN MOLECULAR BIOLOGY* (1986) and Sambrook et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the Novel 7TM receptor (H2CAA71) polypeptide is to be expressed for use in screening assays, generally, it is preferred that the polypeptide be produced at the surface of the cell. In this event, the cells may be harvested prior to use in the screening assay. If Novel 7TM receptor (H2CAA71) polypeptide is secreted into the medium, the medium can be recovered in order to recover and purify the polypeptide; if produced intracellularly, the cells must first be lysed before the polypeptide is recovered.

Novel 7TM receptor (H2CAA71) polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of Novel T7M receptor (H2CAA71) polynucleotides for use as diagnostic reagents. Detection of a mutated form of Novel 7TM receptor (H2CAA71) gene associated with a dysfunction will provide a diagnostic tool that can add to or define a diagnosis of a disease or susceptibility to a disease which results from under-expression, over-expression or altered expression of Novel 7TM receptor (H2CAA71). Individuals carrying mutations in the Novel 7TM receptor (H2CAA71) gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled Novel 7TM receptor (H2CAA71) nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et aL, *Proc Natl Acad Sci USA* (1985) 85: 4397–4401. In another embodiment, an array of oligonucleotides probes comprising Novel 7TM receptor (H2CAA71) nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; bury retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome through detection of mutation in the Novel 7TM receptor (H2CAA71) gene by the methods described.

In addition, infections such as bacterial, fungal, protozoan and viral infections, particularly infections caused by HIV-1 or HIV-2; pain; cancers; anorexia; bulimia. asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, can be diagnosed by methods comprising determining from a sample derived from a subject an abnormally decreased or increased level of Novel 7TM receptor (H2CAA71) polypeptide or Novel 7TM receptor (H2CAA71) mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an Novel 7TM receptor (H2CAA7 1), in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their figments or analogs thereof, or cells expressing them can also be used as immunogens to produce antibodies immunospecific for the Novel 7TM receptor (H2CAA71) polypeptides. The term "immunospecific" means that the antibodies have substantial greater affinity for the polypeptides of the invention than their affinity for other related polypeptides in the prior art.

Antibodies generated against the Novel 7TM receptor (H2CAA71) polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Koher, G. and Milstein, C., Nature (1975)256:495–497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against Novel 7TM receptor (H2CAA71) polypeptides may also be employed to treat infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

Vaccines

Another aspect of the invention relates to a method for inducing an immunological response in a mammal which comprises inoculating the mammal with Novel 7TM receptor (H2CAA71) polypeptide, or a fragment thereof, adequate to produce antibody and/or T cell immune response to protect said animal from infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. Yet another aspect of the invention relates to a method of inducing immunological response in a mammal which comprises, delivering Novel 7TM receptor (H2CAA71) polypeptide via a vector directing expression of Novel 7TM receptor (H2CAA7 1) polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a Novel 7TM receptor (H2CAA71) polypeptide wherein the composition comprises a Novel TIM receptor (H2CAA71) polypeptide or Novel 7TM receptor (H2CAA71) gene. The vaccine formulation may further comprise a suitable carrier. Since Novel 7TM receptor (H2CAA71) polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The Novel 7TM receptor (H2CAA7 1) polypeptide of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et aL, Current Protocols in Immunology 1(2):Chapter 5 (1991).

Novel 7TM receptor (H2CAA71) polypeptides are responsible for many biological functions, including many pathologies. Accordingly, it is desirous to find compounds and drugs which stimulate Novel 7TM receptor (H2CAA71) on the one hand and which can inhibit the function of Novel 7TM receptor (H2CAA7 1) on the other hand. In general, agonists are employed for therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome. Antagonists may be employed for a variety of therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma, allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

In general, such screening procedures involve producing appropriate cells which express the receptor polypeptide of the present invention on the surface thereof Such cells include cells from mammals, yeast, Drosophila or E coli. Cells expressing the receptor (or cell membrane containing the expressed receptor) are then contacted with a test compound to observe binding, or stimulation or inhibition of a functional response.

One screening technique includes the use of cells which express receptor of this invention (for example, transfected CHO cells) in a system which measures extracellular pH or intracellular calcium changes caused by receptor activation. In this technique, compounds may be contacted with cells expressing the receptor polypeptide of the present invention. A second messenger response, e.g., signal transduction, pH changes, or changes in calcium level, is then measured to determine whether the potential compound activates or inhibits the receptor.

Another method involves screening for receptor inhibitors by determining inhibition or stimulation of receptor-mediated cAMP and/or adenylate cyclase accumulation. Such a method involves transfecting a eukaryotic cell with the receptor of this invention to express the receptor on the cell surface. The cell is then exposed to potential antagonists in the presence of the receptor of this invention. The amount of cAMP accumulation is then measured. If the potential antagonist binds the receptor, and thus inhibits receptor binding, the levels of receptor-mediated cAMP, or adenylate cyclase, activity will be reduced or increased.

Another methods for detecting agonists or antagonists for the receptor of the present invention is the yeast based technology as described in U.S. Pat. 5,482,835 which is incorporated herein by reference.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed.

The Novel 7TM receptor (H2CAA71) cDNA, protein and antibodies to the protein may also be used to configure assays for detecting the effect of added compounds on the production of Novel 7TM receptor (H2CAA71) mRNA and protein in cells. For example, an ELISA may be constructed for measuring secreted or cell associated levels of Novel 7TM receptor (H2CAA71) protein using monoclonal and polyclonal antibodies by standard methods known in the art, and this can be used to discover agents which may inhibit or enhance the production of Novel 7TM receptor (H2CAA71) (also called antagonist or agonist, respectively) from suitably manipulated cells or tissues. Standard methods for conducting screening assays are well understood in the art.

Examples of potential Novel 7TM receptor (H2CAA71) antagonists include antibodies or, in some cases, oligonucleotides or proteins which are closely related to the ligand of the Novel 7TM receptor (H2CAA71), e.g., a fragment of the ligand, or small molecules which bind to the receptor but do not elicit a response, so that the activity of the receptor is prevented.

Prophylactic and Therapeutic Methods

This invention provides methods of treating abnormal conditions such as, infections such as bacterial, fungal, protozoan and viral infections, particularly infections caused by HIV-1 or HIV-2; pain; cancers; anorexia; bulimia; asthma; Parkion's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, related to both an excess of and insufficient amounts of Novel 7TM receptor (H2CAA71) activity.

If the activity of novel 7TM receptor (H2CAA71) is in excess, several approaches are available. One approach comprises administering to a subject an inhibitor compound (antagonist) as hereinabove described along with a pharmaceutically acceptable carrier in an amount effective to inhibit activation by blocking binding of ligands to the Novel 7TM receptor (H2CAA71), or by inhibiting a second signal, and thereby alleviating the abnormal condition. In another approach, soluble forms of Novel 7TM receptor (H2CAA71) polypeptides still capable of binding the ligand in competition with endogenous Novel 7TM receptor (H2CAA71) may be administered. Typical embodiments of such competitors comprise fragments of the Novel 7TM receptor (H2CAA71) polypeptide.

In still another approach, expression of the gene encoding endogenous Novel 7TM receptor (H2CAA71) can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al, *Science* (1991) 251:1360. These oligomers can be administered per se or the relevant oligomers can be expressed in vivo.

For treating abnormal conditions related to an underexpression of Novel 7TM receptor (H2CAA71) and its activity, several approaches are also available. One approach comprises administering to a subject a therapeutically effective amount of a compound which activates Novel 7TM receptor (H2CAA71), i.e., an agonist as described above, in combination with a pharmaceutically acceptable carrier, to thereby alleviate the abnormal condition. Alternatively, gene therapy may be employed to effect the endogenous production of Novel 7TM receptor (H2CAA71) by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of Novel 7TM receptor (H2CAA71) polypeptides in combination with a suitable pharmaceutical carrier.

Formulation and Administration

Peptides, such as the soluble form of Novel 7TM receptor (H2CAA71) polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

Gene Cloning

The H2CAA71 EST (#898510) was identified from the Human Genome Sciences (HGS) database as a potential 7TM receptor and has the following sequence:

```
  1 GGCACGAGAA  CGCCATCATT  AGGATTCACT  GTAACGTTAG  TGCTATTAAA
 51 CTCACTAGCA  TTTTTATTAA  TGGCCGTTAT  CTACACTAAG  CTATACTGCA
101 ACTTGGAAAA  AGAGGACCTC  TCAGAAAACT  CACAATCTAG  CATGATTAAG
151 CATGTCGCTT  GGCTAATCTT  CACCAATTGC  ATCTTTTTCT  GCCCTGTGGC
201 GTTTTTTTCA  TTTGCACCAT  TGATCACTGC  AATCTCTATC  AGCCCCGAAA
251 TAATGAAGTC  TGTTACTCTG  ATATTTTTTC  CATTGCCTGC  TTGCCTGAAT
301 CCAGTCCTGT  ATGTTTTCTT  CAACCCAAAG  TTTAAAGAGG  ACTGGGAAGT
351 TACTGAGGCG  ACGTGTTTAC  CAGGAAAAGT  GGGTCCAGTT  TCAGTTNCCN
401 CATAGNCCAG  GTGGTTTCTG  GAACAGGGTT  TNTATAGGGT  TTGGGATGTA
451 CTCACATTNG  AAGGCAACCT  GAC   (SEQ ID NO:3)
```

This clone was ordered and sequenced completely. Analysis of the sequence revealed that the clone is a truncated clone. Therefore, oligonucleotides (5') were designed at the 5' end of the clone. This oligo was: AGTTAGGATGCCAGTATA-GATTCCC (SEQ ID NO:4). This oligo was used to PCR a 1.3 kb 5' fragment using the Marathon technique (Cloneteck). The 5' PCR fragment was subcloned into pCR2.1 vector and were sequenced. This fragment was found to overlap with the original H2CAA71 truncated clone. The full length clone is of 4.2 kb in length and it encodes a protein of 644 amino acids.

Example 2

Mammalian Cell Expression

The receptors of the present invention are expressed in either human embryonic kidney 293 HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/m C418. After 3 weeks of selection, individual clones are picked and expanded for further analysis. REK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G418-resistant clones analyzed.

Example 3

Ligand bank for binding and functional assays.

A bank of over 200 putative receptor ligands has been assembled for screening. The bank composes: transmitters, hormones and chemokines known to act via a human seven transmembrane (7TM) receptor; naturally occurring compounds which may be putative agonists for a human 7TM receptor, non-mammalian, biologically active peptides for which a mammialian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc., see below) as well as binding assays.

Example 4
Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 5
Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/mi. Ovarian lobes are removed from adult female toads, Stage V defolliculated oocytes are obtained, and RNA transcripts (10 ng/oocytc) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

Example 6
Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 7
Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify'natural ligands. Extracts that produce positive functional responses can be sequentially subfractionated until an activating ligand is isolated identified.

Example 8
Calcium and cAMP Functional Assays

7TM receptors which are expressed in HEK 293 cells have been shown to be coupled functionally to activation of PLC and calcium mobilization and/or cAMP stimulation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day >150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP fluctuation are tested in vector control cells to determine if the response is unique to the transfected cells expressing receptor.

---

What is claimed is:

1. An isolated polynucleotide comprising a nucleotide sequence encoding the polypeptide having the amino acid sequence set forth in SEQ ID NO 2.

2. The isolated polynucleotide of claim 1 wherein said polynucleotide is an RNA transcript of the entire length of SEQ ID NO:1.

3. The isolated polynucleotide of claim 1 wherein said polynucleotide is an RNA transcript of the entire coding region of SEQ ID NO:1.

4. An isolated polynucleotide obtainable by screening an appropriate library under stringent hybridization conditions with a probe having the sequence of a polynucleotide encoding the polypeptide set forth in SEQ ID NO:2 wherein said isolated polynucleotide encodes a human H2CAA71 protein.

5. The isolated polynucleotide of claim 4 wherein said sequence comprises SEQ ID NO:1.

6. An isolated probe comprising a nucleotide sequence encoding a polypeptide having the amino acid sequence set forth in SEQ ID NO:2 wherein the nucleotide sequence comprise up to a total of 5 nucleotide alterations, wherein said alterations include deletions, substitutions, or insertions for each 100 nucleotides of the nucleotide sequence.

7. The probe of claim 6 comprising the nucleotide sequence set forth in SEQ ID NO:1 wherein the nucleotide sequence comprises up to a total of 5 nucleotide alterations for each 100 nucleotides of the nucleotide sequence, wherein said alterations include deletions, substitutions, or insertions.

8. The isolated polynucleotide of any one of claims 1, 4, 5, 6, and 7 which is DNA or RNA.

9. An isolated polynucleotide comprising a nucleotide sequence which is the entire coding region of the polynucleotide sequence set forth in SEQ ID NO:1.

10. An isolated polynucleotide comprising the polynucleotide sequence set forth in SEQ ID NO:1.

11. An isolated polynucleotide which is complementary to any one of the isolated polynucleotides of claims 9, 10, 1–5, 6, and 7.

12. An expression vector comprising a nucleic acid encoding a polypeptide comprising the amino acid sequence set forth in SEQ ID NO:2.

13. An isolated host cell transformed with the expression vector of claim 12.

14. A cell membrane of the host cell of claim 13 expressing a polypeptide comprising the amino acid sequence set forth in SEQ ID NO:2.

15. A process for producing a polypeptide having the amino acid sequence set forth in SEQ ID NO:2 comprising culturing the host cell of claim 13 under conditions sufficient for the production of said polypeptide and recovering said polypeptide from the culture.

16. A process for producing a cell which produces a polypeptide having the amino acid sequence set forth in SEQ ID NO:2 comprising transforming or transfecting a host cell with the expression vector of claim 2 such that the host cell, under appropriate culture conditions, produces said polypeptide.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 4203 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GCTTCCATCC   TAATACAACT   CACTATAGGG   CTCGAGCGGC   CGCCCGGGCA   GGTGCTTGAC      60

GGAGGTGCCT   GTGCACCCCC   TCAGCAATCT   GCCCACCCTA   CAGGCGCTGA   CCCTGGCTCT     120

CAACAAGATC   TCAAGCATCC   CTGACTTTGC   ATTTACCAAC   CTTTCAAGCC   TGGTAGTTCT     180

GCATCTTCAT   AACAATAAAA   TTAGAAGCCT   GAGTCAACAC   TGTTTTGATG   GACTAGATAA     240

CCTGGAGACC   TTAGACTTGA   ATTATAATAA   CTTGGGGGAA   TTTCCTCAGG   CTATTAAAGC     300
```

```
CCTTCCTAGC CTTAAAGAGC TAGGATTTCA TAGTAATTCT ATTTCTGTTA TCCCTATGGA    360
GCATTTGATG GTAATCCACT CTTAAGAACT ATACATTTGT ATGATAATCC TCTGTCTTTT    420
GTGGGGAACT CAGCATTTCA CAATTTATCT GATCTTCATT CCCTAGTCAT TCGTGGTGCA    480
AGCATGGTGC AGCAGTTCCC CAATCTTACA GGAACTGTCC ACCTGGAAAG TCTGACTTTG    540
ACAGGTACAA AGATAAGCAG CATACCTAAT AATTTGTGTC AAGAACAAAA GATGCTTAGG    600
ACTTTGGACT TGTCTTACAA TAATATAAGA GACCTTCCAA GTTTTAATGG TTGCCATGCT    660
CTGGAAGAAA TTTCTTTACA GCGTAATCAA ATCTACCAAA TAAAGGAAGG CACCTTTCAA    720
GGCCTGATAT CTCTAAGGAT TCTAGATCTG AGTAGAAACC TGATACATGA AATTCACAGT    780
AGAGCTTTTG CCACACTTGG GCCAATAACT AACCTAGATG TAAGTTTCAA TGAATTAACT    840
TCCTTTCCTA CGGAAGGCCT GAATGGGCTA AATCAACTGA AACTGGTGGG CAACTTCAAG    900
CTGAAAGAAG CCTTAGCAGC AAAAGACTTT GTTAACCTCA GGTCTTATC AGTACCATAT     960
GCTTATCAGT GCTGTGCATT TTGGGGTTGT GACTCTTATG CAAATTTAAA CACAGAAGAT    1020
AACAGCCTCC AGGACCACAG TGTGGCACAG GAGAAAGGTA CTGCTGATGC AGCAAATGTC    1080
ACAAGCACTC TTGAAAATGA AGAACATAGT CAAATAATTA TCCATTGTAC ACCTTCAACA    1140
GGTGCTTTTA AGCCCTGTGA ATATTTACTG GGAAGCTGGA TGATTCGTCT TACTGTGTGG    1200
TTCATTTTCT TGGTTGCATT ATTTTTCAAC CTGCTTGTTA TTTTAACAAC ATTTGCATCT    1260
TGTACATCAC TGCCTTCGTC CAAATTGTTT ATAGGCTTGA TTTCTGTGTC TAACTTATTC    1320
ATGGGAATCT ATACTGGCAT CCTAACTTTT CTTGATGCTG TGTCCTGGGG CAGATTCGCT    1380
GAATTTGGCA TTTGGTGGGA AACTGGCAGT GGCTGCAAAG TAACTGGGTT TCTTGCAGTT    1440
TTCTCCTCAG AAAGTGCCAT ATTTTTATTA ATGCTAGCAA CTGTCGAAAG AAGCTTATCT    1500
GCAAAGATA TAATGAAAAA TGGGAAGAGC AATCATCTCA AACAGTTCCG GGTTGCTGCC     1560
CTTTTGGCTT TCCTAGGTGC TACAGTAACA GGCTGTTTTC CCCTTTTCCA TAGAGGGGAA    1620
TATTCTGCAT CACCCCTTTG TTTGCCATTT CCTACAGGTG AAACGCCATC ATTAGGATTC    1680
ACTGTAACGT TAGTGCTATT AAACTCACTA GCATTTTTAT TAATGGCCGT TATCTACACT    1740
AAGCTATACT GCAACTTGGA AAAAGAGGAC CTCTCAGAAA ACTCACAATC TAGCATGATT    1800
AAGCATGTCG CTTGGCTAAT CTTCACCAAT TGCATCTTTT TCTGCCCTGT GGCGTTTTTT    1860
TCATTTGCAC CATTGATCAC TGCAATCTCT ATCAGCCCCG AAATAATGAA GTCTGTTACT    1920
CTGATATTTT TTCCATTGCC TGCTTGCCTG AATCCAGTCC TGTATGTTTT CTTCAACCCA    1980
AAGTTTAAAG AAGACTGGAA GTTACTGAAG CGACGTGTTA CCAAGAAAAG TGGATCAGTT    2040
TCAGTTTCCA TCAGTAGCCA AGGTGGTTGT CTGGAACAGG ATTTCTACTA CGACTGTGGC    2100
ATGTACTCAC ATTTGCAGGG CAACCTGACT GTTTGCGACT GCTGCGAATC GTTTCTTTTA    2160
ACAAAGCCAG TATCATGCAA ACACTTGATA AAATCACACA GCTGTCCTGC ATTGGCAGTG    2220
GCTTCTTGCC AAAGACCTGA GGGCTACTGG TCCGACTGTG GCACACAGTC GGCCCACTCT    2280
GATTATGCAG ATGAAGAAGA TTCCTTTGTC TCAGACAGTT CTGACCAGGT GCAGGCCTGT    2340
GGACGAGCCT GCTTCTACCA GAGTAGAGGA TTCCCTTTGG TGCGCTATGC TTACAATCTA    2400
CCAAGAGTTA AAGACTGAAC TACTGTGTGT GTAACGTTT CCCCCGTCAA CCAAAATCAG     2460
TGTTTATAGA GTGAACCCTA TTCTCATCTT TCATCTGGGA AGCACTTCTG TAATCACTGC    2520
CTGGTGTCAC TTAGAAGAAG GAGAGGTGGC AGTTTATTTC TCAAACCAGT CATTTTCAAA    2580
GAACAGGTGC CTAAATTATA AATTGGTGAA AAATGCAATG TCCAAGCAAT GTATGATCTG    2640
TTTGAAACAA ATATATGACT TGAAAAGGAT CTTAGGTGTA GTAGAGCAAT ATAATGTTAG    2700
```

-continued

```
TTTTTTCTGA  TCCATAAGAA  GCAAATTTAT  ACCTATTTGT  GTATTAAGCA  CAAGATAAAG   2760

AACAGCTGTT  AATATTTTTT  AAAATCTAT   TTTAAAATGT  GATTTTCTAT  AACTGAAGAA   2820

AATATCTTGC  TAATTTTACC  TAATGTTTCA  TCCTTAATCT  CAGGACAACT  TACTGCAGGG   2880

CCAAAAAAGG  GACTGTCCCA  GCTAGAACTG  TGAGAGTATA  CATAGGCATT  ACTTTATTAT   2940

GTTTTCACTT  GCCATCCTTG  ACATAAGAGA  ACTATAAATT  TTGTTTAAGC  AATTTATAAA   3000

TCTAAAACCT  GAAGATGTTT  TTAAAACAAT  ATTAACAGCT  GTTAGGTTAA  AAAAATAGCT   3060

GGACATTTGT  TTTCAGTCAT  TATACATTGC  TTTGGTCCAA  TCAGTAATTT  TTTCTTAAGT   3120

GTTTTGTGAT  TACACTACTA  GAAAAAAAGT  AAAAGGCTAA  TTGCTGTGTG  GGTTTAGTCG   3180

ATTTGGCTAA  ACTACTAACT  AATGTGGGGG  TTTAATAGTA  TCTGAGGGAT  TTGGTGGCTT   3240

CATGTAATGT  TCTCATTAAT  GAATACTTCC  TAATATCGTT  GGCTCTACTA  ATATTTTCCA   3300

ATTTGCTGGG  ATGTCACCTA  GCAATAGCTT  GGATTATATA  GAAAGTAAAC  TGTGGTCAAT   3360

ACTTGCATTT  AATTAGACGA  AACGGGGAGT  AATTATGACA  CGAAGTACTT  ATGTTTATTT   3420

CTTAGTGAGC  TGGATTATCT  TGAACCTGTG  CTATTAAATG  GAAATTTCCA  TACATCTTCC   3480

CCATACTATT  TTTTATAAAA  GAGCCTATTC  AATAGCTCAG  AGGTTGAACT  CTGGTTAAAC   3540

AAGATAATAT  GTTATTAATA  AAAATAGAAG  AAGAAAGAAT  AAAGCTTAGT  CCTGTGTCTT   3600

TAAAAATTAA  AAATTTTACT  TGATTCCCAT  CTATGGGCTT  TAGACCTATT  ACTGGGTGGA   3660

GTCTTAAAGT  TATAATTGTT  CAATATGTTT  TTTGAACAGT  GTGCTAAATC  AATAGCAAAC   3720

CCACTGCCAT  ATTAGTTATT  CTGAATATAC  TAAAAAAATC  CAGCTAGATT  GCAGTTTAAT   3780

AATTAAACTG  TACATACTGT  GCATATAATG  AATTTTTATC  TTATGTAAAT  TATTTTTAGA   3840

ACACAAGTTG  GGAAATGTGG  CTTCTGTTCA  TTTCGTTTAA  TTAAAGCTAC  CTCCTAAACT   3900

ATAGTGGCTG  CCAGTAGCAG  ACTGTTAAAT  TGTGGTTTAT  ATACTTTTTG  CATTGTAAAT   3960

AGTCTTTGTT  GTACATTGTC  AGTGTAATAA  AAACAGAATC  TTTGTATATC  AAAATCATGT   4020

AGTTTGTATA  AAATGTGGGA  AGGATTTATT  TACAGTGTGT  TGTAATTTTG  TAAGGCCAAC   4080

TATTTACAAG  TTTTAAAAAT  TGCTATCATG  TATATTTACA  CATCTGATAA  ATATTAAATC   4140

ATAACTTGGT  AAGAAACTCC  TAATTAAAAG  GTTTTTTCCA  AAAAAAAAA   AAAAAAAAA   4200

AAA                                                                     4203
```

( 2 ) INFORMATION FOR SEQ ID NO:2:

( i ) SEQUENCE CHARACTERISTICS:
        ( A ) LENGTH: 644 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met  Val  Gln  Gln  Phe  Pro  Asn  Leu  Thr  Gly  Thr  Val  His  Leu  Glu  Ser
 1                  5                  10                      15

Leu  Thr  Leu  Thr  Gly  Thr  Lys  Ile  Ser  Ser  Ile  Pro  Asn  Asn  Leu  Cys
            20                      25                      30

Gln  Glu  Gln  Lys  Met  Leu  Arg  Thr  Leu  Asp  Leu  Ser  Tyr  Asn  Asn  Ile
        35                      40                      45

Arg  Asp  Leu  Pro  Ser  Phe  Asn  Gly  Cys  His  Ala  Leu  Glu  Glu  Ile  Ser
        50                      55                      60

Leu  Gln  Arg  Asn  Gln  Ile  Tyr  Gln  Ile  Lys  Glu  Gly  Thr  Phe  Gln  Gly
65                       70                      75                      80
```

| | | | | | | | | | | | | | | |
|---|---|---|---|---|---|---|---|---|---|---|---|---|---|---|
| Leu | Ile | Ser | Leu | Arg<br>85 | Ile | Leu | Asp | Leu | Ser<br>90 | Arg | Asn | Leu | Ile | His<br>95 | Glu |

Leu Ile Ser Leu Arg Ile Leu Asp Leu Ser Arg Asn Leu Ile His Glu
                    85                  90                  95

Ile His Ser Arg Ala Phe Ala Thr Leu Gly Pro Ile Thr Asn Leu Asp
            100             105             110

Val Ser Phe Asn Glu Leu Thr Ser Phe Pro Thr Glu Gly Leu Asn Gly
        115             120             125

Leu Asn Gln Leu Lys Leu Val Gly Asn Phe Lys Leu Lys Glu Ala Leu
    130             135             140

Ala Ala Lys Asp Phe Val Asn Leu Arg Ser Leu Ser Val Pro Tyr Ala
145             150             155             160

Tyr Gln Cys Cys Ala Phe Trp Gly Cys Asp Ser Tyr Ala Asn Leu Asn
                165             170             175

Thr Glu Asp Asn Ser Leu Gln Asp His Ser Val Ala Gln Glu Lys Gly
            180             185             190

Thr Ala Asp Ala Ala Asn Val Thr Ser Thr Leu Glu Asn Glu Glu His
        195             200             205

Ser Gln Ile Ile Ile His Cys Thr Pro Ser Thr Gly Ala Phe Lys Pro
    210             215             220

Cys Glu Tyr Leu Leu Gly Ser Trp Met Ile Arg Leu Thr Val Trp Phe
225             230             235             240

Ile Phe Leu Val Ala Leu Phe Phe Asn Leu Val Ile Leu Thr Thr
                245             250             255

Phe Ala Ser Cys Thr Ser Leu Pro Ser Ser Lys Leu Phe Ile Gly Leu
            260             265             270

Ile Ser Val Ser Asn Leu Phe Met Gly Ile Tyr Thr Gly Ile Leu Thr
        275             280             285

Phe Leu Asp Ala Val Ser Trp Gly Arg Phe Ala Glu Phe Gly Ile Trp
    290             295             300

Trp Glu Thr Gly Ser Gly Cys Lys Val Thr Gly Phe Leu Ala Val Phe
305             310             315             320

Ser Ser Glu Ser Ala Ile Phe Leu Leu Met Leu Ala Thr Val Glu Arg
                325             330             335

Ser Leu Ser Ala Lys Asp Ile Met Lys Asn Gly Lys Ser Asn His Leu
            340             345             350

Lys Gln Phe Arg Val Ala Ala Leu Ala Phe Leu Gly Ala Thr Val
        355             360             365

Thr Gly Cys Phe Pro Leu Phe His Arg Gly Glu Tyr Ser Ala Ser Pro
    370             375             380

Leu Cys Leu Pro Phe Pro Thr Gly Glu Thr Pro Ser Leu Gly Phe Thr
385             390             395             400

Val Thr Leu Val Leu Leu Asn Ser Leu Ala Phe Leu Leu Met Ala Val
                405             410             415

Ile Tyr Thr Lys Leu Tyr Cys Asn Leu Glu Lys Glu Asp Leu Ser Glu
            420             425             430

Asn Ser Gln Ser Ser Met Ile Lys His Val Ala Trp Leu Ile Phe Thr
        435             440             445

Asn Cys Ile Phe Phe Cys Pro Val Ala Phe Phe Ser Phe Ala Pro Leu
    450             455             460

Ile Thr Ala Ile Ser Ile Ser Pro Glu Ile Met Lys Ser Val Thr Leu
465             470             475             480

Ile Phe Phe Pro Leu Pro Ala Cys Leu Asn Pro Val Leu Tyr Val Phe
                485             490             495

Phe Asn Pro Lys Phe Lys Glu Asp Trp Lys Leu Leu Lys Arg Arg Val

|     |     |     | 500 |     |     |     | 505 |     |     |     | 510 |     |     |     |
|-----|-----|-----|-----|-----|-----|-----|-----|-----|-----|-----|-----|-----|-----|-----|
| Thr | Lys | Lys 515 | Ser | Gly | Ser | Val 520 | Ser | Val | Ile | Ser | Ser 525 | Gln | Gly | Gly |
| Cys | Leu 530 | Glu | Gln | Asp | Phe | Tyr 535 | Tyr | Asp | Cys | Gly | Met 540 | Tyr | Ser | His | Leu |
| Gln 545 | Gly | Asn | Leu | Thr | Val 550 | Cys | Asp | Cys | Cys | Glu 555 | Ser | Phe | Leu | Leu | Thr 560 |
| Lys | Pro | Val | Ser | Cys 565 | Lys | His | Leu | Ile | Lys 570 | Ser | His | Ser | Cys | Pro 575 | Ala |
| Leu | Ala | Val | Ala 580 | Ser | Cys | Gln | Arg | Pro 585 | Glu | Gly | Tyr | Trp | Ser 590 | Asp | Cys |
| Gly | Thr | Gln 595 | Ser | Ala | His | Ser | Asp 600 | Tyr | Ala | Asp | Glu | Glu 605 | Asp | Ser | Phe |
| Val | Ser | Asp 610 | Ser | Ser | Asp | Gln 615 | Val | Gln | Ala | Cys | Gly 620 | Arg | Ala | Cys | Phe |
| Tyr 625 | Gln | Ser | Arg | Gly | Phe 630 | Pro | Leu | Val | Arg | Tyr 635 | Ala | Tyr | Asn | Leu | Pro 640 |
| Arg | Val | Lys | Asp |

( 2 ) INFORMATION FOR SEQ ID NO:3:

( i ) SEQUENCE CHARACTERISTICS:
        ( A ) LENGTH: 473 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

| GGCACGAGAA | CGCCATCATT | AGGATTCACT | GTAACGTTAG | TGCTATTAAA | CTCACTAGCA | 60 |
| TTTTTATTAA | TGGCCGTTAT | CTACACTAAG | CTATACTGCA | ACTTGGAAAA | AGAGGACCTC | 120 |
| TCAGAAAACT | CACAATCTAG | CATGATTAAG | CATGTCGCTT | GGCTAATCTT | CACCAATTGC | 180 |
| ATCTTTTTCT | GCCCTGTGGC | GTTTTTTTCA | TTTGCACCAT | TGATCACTGC | AATCTCTATC | 240 |
| AGCCCCGAAA | TAATGAAGTC | TGTTACTCTG | ATATTTTTC | CATTGCCTGC | TTGCCTGAAT | 300 |
| CCAGTCCTGT | ATGTTTTCTT | CAACCCAAAG | TTTAAAGAGG | ACTGGGAAGT | TACTGAGGCG | 360 |
| ACGTGTTTAC | CAGGAAAAGT | GGGTCCAGTT | TCAGTTNCCN | CATAGNCCAG | GTGGTTTCTG | 420 |
| GAACAGGGTT | TNTATAGGGT | TTGGGATGTA | CTCACATTNG | AAGGCAACCT | GAC | 473 |

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

| AGTTAGGATG | CCAGTATAGA | TTCCC | 25 |